United States Patent
Camara-Ferrer et al.

(10) Patent No.: US 9,176,119 B2
(45) Date of Patent: Nov. 3, 2015

(54) METHOD FOR QUANTIFYING A CHOLINERGIC NEUROTOXIN IN A SAMPLE

(75) Inventors: José-Antonio Camara-Ferrer, Paris (FR); Michael Auguet, Palaiseau (FR); Pierre-Etienne Chabrier De Lassauniere, Paris (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 1736 days.

(21) Appl. No.: 12/065,523

(22) PCT Filed: Aug. 11, 2006

(86) PCT No.: PCT/FR2006/001944
§ 371 (c)(1),
(2), (4) Date: Mar. 3, 2008

(87) PCT Pub. No.: WO2007/026061
PCT Pub. Date: Mar. 8, 2007

(65) Prior Publication Data
US 2008/0247952 A1    Oct. 9, 2008

(30) Foreign Application Priority Data
Sep. 1, 2005    (FR) .................. 0508974

(51) Int. Cl.
*A61K 49/00*    (2006.01)
*A61K 49/06*    (2006.01)
*G01N 33/50*    (2006.01)

(52) U.S. Cl.
CPC ........ *G01N 33/5088* (2013.01); *G01N 2333/33* (2013.01); *G01N 2333/4603* (2013.01)

(58) Field of Classification Search
None
See application file for complete search history.

(56) References Cited

U.S. PATENT DOCUMENTS

| | | | |
|---|---|---|---|
| 8,273,359 B2 | 9/2012 | Favre | |
| 2004/0147030 A1 | 7/2004 | Nebert | |
| 2006/0143718 A1 | 6/2006 | Nebert | |
| 2011/0152198 A1 | 6/2011 | Hunt | |

FOREIGN PATENT DOCUMENTS

| | | |
|---|---|---|
| GB | 2419526 | 5/2005 |
| WO | 99/42606 | 8/1999 |
| WO | 01/26736 | 4/2001 |
| WO | 01/58472 | 8/2001 |
| WO | 03/013234 | 2/2003 |
| WO | 2005/082339 | 9/2005 |
| WO | 2006/005910 | 1/2006 |
| WO | 2007/026061 | 3/2007 |

OTHER PUBLICATIONS

Bhattacharya et al. J Pharm Exp Ther 311: 92-98, 2004.*
Gibb et al (SICB Meeting Abstract, dated Jan. 7, 2005).*
O'Neill and Gibb, Physiol Biochem Zool 80: 241-249, 2007.*
Ray et al. Walter Reed Army Inst of Research Washington DC, Report dated May 13, 1993.*
Ashton et al (Toxicon 23: 235-246, 1985).*
Holmberg et al J Experim Biol 207: 4085-4094, 2004.*
International Search Report of PCT/FR2006/001944.
Written Opinion of PCT/ FR2006/001944 I.
Pearce et al., "Pharmacological characterization of botulinum toxin for basic science and medicine," Toxicon, vol. 35, No. 9, 1997, pp. 1373-1412, XP002282904.
Behra et al., "The use of zebrafish mutants to identify secondary target effects of acetylcholine esterase inhibitors," Toxicological Sciences, vol. 77, No. 2, (Feb. 2004), pp. 325-333, XP002393925.
Hill et al., "Zebrafish as a model vertebrate for investigating chemical toxicity," Toxicological Sciences, vol. 86, No. 1, (Jul. 2005), pp. 6-19, XP002393924.
Krone et al., "Use of fish liver PLHC-1 cells and zebrafish embryos in cytotoxicity assays," Methods: A Companion to Methods in Enzymology, vol. 35, No. 2, (Feb. 2005), pp. 176-187, XP004762302.
Sheridan et al., "Comparison of in vivo and in vitro mouse bioassays for botulinum toxin antagonists," Journal of Applied Toxicology, vol. 19, No. SUPPL1, (Dec. 1999), pp. S29-S33, XP002282903.
Pearce et al., "The Median Paralysis Unit: A more Pharmacologically relevant unit of biologic activity for botulinum toxin," Toxicon, vol. 33, No. 2, 1995, pp. 217-227, XP000601608.
International Preliminary Report on Patentability regarding PCT/FR2006/001944, dated Nov. 8, 2006.
"Botulinum toxin" entry from Wikipedia, the free encyclopedia of Oct. 20, 2011.
Argoff (2002) *The Clinical Journal of Pain* 18: S177-S181.
Calabrese & Resztak (1998) *Expert Opinion on Investigational Drugs* 7(12): 2043-2060.
Gonzalez-Duarte, et al. (2006) *The PRN Notebook* 11(2): 24-29.
Klein (2004) *Dermatol Surg* 30: 452-455.
Canadian Centre for Occupational Health and Safety "What is an $LD_{50}$ and $LC_{50}$." OSH Answers. (2005).
Sesardic & Das *Proc. 6th World Congress on Alternatives & Animal Use in the Life Sciences* AATEX Special Issue 581-585 (2007).

* cited by examiner

*Primary Examiner* — Daniel E Kolker
*Assistant Examiner* — Aditi Dutt
(74) *Attorney, Agent, or Firm* — Hunton & Williams LLP

(57) ABSTRACT

The invention relates to a method for determining the kinetics of action of a cholinergic neurotoxin as well as a method for determining the quantity of neurotoxin in a sample.

9 Claims, 1 Drawing Sheet

METHOD FOR QUANTIFYING A CHOLINERGIC NEUROTOXIN IN A SAMPLE

CONTINUITY DATA

This application is a national stage application of PCT/1-R2006/001944, filed on Aug. 11, 2006, which in turn claims priority to FR 0508974, filed on Sep. 1, 2005; both of which applications are hereby incorporated by reference in their entirety.

FIELD OF INVENTION

A subject of the present invention is a method for determining the kinetics action of a cholinergic neurotoxin, as well as a method for determining the quantity of neurotoxin in a sample.

BACKGROUND OF INVENTION

The methods for quantifying a cholinergic neurotoxin are currently carried out by measurement of a lethal dose LD50 in rodents, in particular in the mouse or the rat. This is more particularly the case of the detection and measurement method for the biological activity of the botulinum toxin.

Thus, when such a method is used, it involves the sacrifice of numerous mammals, in particular mice or rats.

In order to respond to industrial producers' requirements it has become necessary to find an alternative method to the use of mammals for determining the lethal dose LD50 of cholinergic neurotoxins.

Therefore the problem which the invention seeks to resolve is to provide a new method for determining the kinetics action of a cholinergic neurotoxin, as well as a new method for quantifying a cholinergic neurotoxin.

The inventors have unexpectedly demonstrated that it is possible to use teleostian fish for determining the lethal dose LD50 of cholinergic neurotoxins.

SUMMARY OF THE INVENTION

To this end, the present invention proposes a method for determining the kinetics action of a cholinergic neurotoxin, comprising the following stages:
 (i) administering the cholinergic neurotoxin to at least one teleostian fish;
 (ii) detecting the biological activity of the cholinergic neurotoxin as a function of time.

The present invention also proposes a method for determining a quantity of cholinergic neurotoxin comprising the following stages:
 (i) administering the cholinergic neurotoxin to at least one teleostian fish;
 (ii) detecting the biological activity of the cholinergic neurotoxin;
 (iii) comparing the effect obtained in stage (ii) with the effect obtained with a reference substance;
 (iv) determining the quantity of cholinergic neurotoxin.

The invention offers crucial advantages, in particular in terms of economic cost. The use of teleostian fish enables a significant reduction in costs when quantifying batches of botulinum toxin produced on an industrial scale. In fact, the assay of one batch of botulinum toxin uses the $LD_{50}$ method in mice and requires the sacrifice of approximately 100 mice.

Another advantage of the present invention is that the methods according to the invention are much quicker to implement than the known methods, in particular those using mammals. In fact, development of the effects of the cholinergic neurotoxin is more quickly detectable in the teleostian fish than in the mouse. In the particular case where a neuromuscular paralysis is observed in teleostian fish, this paralysis is reversible and the fish recover normal motility 5 days after administration, while 1 month is required in the mouse to recover motility.

Another advantage of the method for determining the kinetics action of a cholinergic neurotoxin according to the invention is that it enables the duration of action of the neurotoxin to be evaluated, as well as the time it takes for the effects of the neurotoxin to appear.

The invention offers the further advantage that teleostian fish reproduce very quickly and in large quantity. It is therefore possible to obtain a very large number of Individuals in a minimum period of time. For example in the case of the zebra fish, an adult can produce 100 to 200 eggs in one laying, which become fully formed embryos in 48 hours and fully formed adults between 21 and 29 days.

In addition, the embryos of teleostian fish are advantageously an intact, separately independent organism, in comparison with mice embryos which are physically connected to their mother. This advantage enables easier testing of the biological activity of a cholinergic neurotoxin on embryos.

Another advantage of the present invention is that it offers an ethically more acceptable method than those used up to now.

Finally, the invention has the advantage of being able to be implemented in all industries, in particular the pharmaceutical, cosmetics industry as well as in the areas of effluent treatment, anti-pollution measures and hygiene in the wider sense, in particular, daily hygiene, food hygiene (food safety) or occupational hygiene.

Other advantages and characteristics of the invention will appear clearly on reading the description and the following examples, which are given purely as illustration and are not in any way limitative.

DETAILED DESCRIPTION OF THE PREFERRED EMBODIMENTS

To this end the present invention proposes a method for determining the kinetics action of a cholinergic neurotoxin comprising the following stages:
 (i) administering the cholinergic neurotoxin to at least one teleostian fish;
 (ii) detecting the biological activity of the cholinergic neurotoxin as a function of time.

The present invention also proposes a method for determining a quantity of cholinergic neurotoxin comprising the following stages:
 (i) administering the cholinergic neurotoxin to at least one teleostian fish;
 (ii) detecting the biological activity of the cholinergic neurotoxin;
 (iii) comparing the effect obtained in stage (ii) to the effect obtained with a reference substance;
 (iv) determining the quantity of cholinergic neurotoxin.

Advantageously, the method according to the invention can enable an $LD_{50}$ of a cholinergic neurotoxin to be determined.

Within the context of the present invention, by $LD_{50}$ is meant the lethal or semi-lethal dose of a given substance. This is the dose which causes the death of 50% of the animals tested in one group.

The method according to the invention can also allow the biological activity of a cholinergic neurotoxin to be detected. More particularly, the biological activity detectable according to the method of the invention is a neuromuscular activity. Preferably, it is a muscular paralysis. It can be a paralysis of the smooth muscles or a paralysis of the striated muscles. This paralysis can lead to the death of the animal.

The cholinergic neurotoxin administered in stage (i) of the method according to the invention can lead to the death of the animal.

The cholinergic neurotoxin administered in stage (i) of the method according to the invention can be, inter alia, a protein, a polypeptide, a peptide, a fusion protein, a truncated protein, a chimeric protein, a mutated protein or a recombinant protein.

Within the context of the present invention, by protein, polypeptide or peptide is meant a polymer of amino acids, whether natural or otherwise, levorotatory or otherwise, dextrorotatory or otherwise.

Within the context of the present invention, by chimeric protein is meant a protein obtained after combination of different types of molecules, for example after combination of lipids, glycolipids, peptides, polypeptides, proteins, glycoproteins, carbohydrates, polysaccharides, nucleic acids, polyethylene glycol, etc.

Preferably, the protein is in solution.

According to a variant of the method of the invention, the cholinergic neurotoxin administered in stage (i) can be encapsulated by means of at least one vectorization agent, as for example microspheres, nanoparticles, micelles or liposomes.

According to a variant of the method according to the invention, the cholinergic neurotoxin administered in stage (i) can be combined with permeabilizing agents such as salicylates, fatty acids, metal chelation agents in particular EDTA, cationic, anionic or neutral polymers, or can be combined with mucoadhesive or transdermic formulations.

According to a preferential method of the invention, the cholinergic neurotoxin is a clostridial toxin.

Still more preferably, the cholinergic neurotoxin administered in stage (i) is the botulinum toxin, for example the botulinum toxin type A, B, C, D, E, F, or G.

It can in particular be the botulinum toxin type A, including $A_1$, $A_2$, and $A_3$ (Dysport® marketed by Ipsen, or Botox® marketed by Allergan), type B (Myobloc® marketed by Solstice Neurosciences), type C (including $C_1$ and $C_2$), type D, type E, type F or type G.

Preferably, the cholinergic neurotoxin will be chosen from the botulinum toxins of type A, B and F. Still more preferably, it will be chosen from the botulinum toxins of type A and B; in particular, it will be the botulinum toxin of type A.

All types of botulinum toxin can bind with a strong affinity to cholinergic motor neurons, penetrating into them and blocking the release of a neurotransmitter, acetylcholine, in the neuromuscular junction. For example the botulinum toxin of type A and E cleaves the protein SNAP-25 (25 kD) at different sites of the protein. The types B, D, F and G act on the VAMP protein also known as synaptobrevin, each type of toxin cleaving its target at different sites. Finally, the C1 type cleaves both syntaxin and the SNAP-25 protein.

Moreover, the botulinum toxin used according to the method of the invention can be presented in the form of a complex of several compounds, comprising inter alia the botulinum toxin, or can be presented in a free form (i.e. free of any complexing protein). The botulinum toxin can be complexed with proteins which are not toxins: haemagglutinin can be mentioned as an example.

Stage (i) is carried out by administering the cholinergic neurotoxin to at least one teleostian fish.

The administration method can vary, and preferably the cholinergic neurotoxin is administered by injection, more particularly by peripheral injection as for example by parenteral, subcutaneous or intramuscular injection.

Preferably, the cholinergic neurotoxin is injected by intraperitoneal route.

According to a variant of the present invention, it is possible to envisage that the fish are anaesthetized before injection.

It is also possible to administer the cholinergic neurotoxin by immersion, ingestion, or by using the technique of biolistic loading, in which particles containing the cholinergic neurotoxin are projected into the fish, its organs or tissues using a compressed-air gun.

Preferably, the cholinergic neurotoxin is administered in vivo. According to a variant of the method according to the invention it is possible to administer the neurotoxin to at least one organ or at least one tissue of the teleostian fish.

The teleostian fish used in stage (i) can be an embryo, a larva or an adult. Preferably, it is a 5-day-old or 21-day-old fish.

Within the context of the present invention, by larva is meant an individual whose development is between the embryonic stage and the adult stage.

Among teleostian fish which are suitable for the implementation of the present invention, the zebra fish (*Danio rerio*), the puffer fish, the giant rerio or the medaka can be mentioned. A fish with a wild phenotype, a mutant phenotype or a transgenic fish can also be used.

Preferably, a zebra fish is used.

According to a variant of the method according to the invention, one or more teleostian fish are contained in a microtitration well of an automatic device. This advantageously permits automation of the quantification method according to the invention.

It is possible to envisage pre-treatment of the fish used in stage (i). For example it is possible to envisage immersing the fish in a bath containing a potential antagonist to the cholinergic neurotoxin, for example an anti-botulinum toxin antibody or an inhibitor. It can also be envisaged to inject this potential neurotoxin antagonist as a pre-treatment before administration of the neurotoxin.

Stage (ii) of the method according to the invention is carried out by detecting biological activity by means of a signal which is generated. The signal which is generated and detected can be a difference in the behaviour of the fish, a slowing of mobility, a reduction in motility; immobility or death of the fish.

Within the context of the present invention, by motility is meant the potential for mobility. Motility comprises all those factors defining the potential for spatial mobility: physical abilities, the impulse to remain still or to be mobile, learnt behaviour. Motility can be transformed into motion, thus making use of various types of mobilities.

Preferably, stage (ii) of the method according to the invention is carried out by detecting biological activity using an image analyzer.

Stage (iii) is carried out by comparing the effect obtained in stage (ii) to the effect obtained with a reference substance.

By reference substance is meant a standard substance, or a substance which has been quantified by a reference method. In general, this is a cholinergic neurotoxin the concentration of which has been determined previously.

Preferably, the reference substance is a clostridial toxin of a known concentration, more particularly it is a botulinum toxin, for example botulinum toxin of type A, B, C, D, E, F or G.

By reference botulinum toxin is meant a botulinum toxin which has been quantified, for example by a different method to that of the invention, or also by a reference method. More particularly, it is a botulinum toxin, the concentration of which has been determined previously.

Stage (iv) of the method according to the invention is carried out by determining the quantity of cholinergic neurotoxin. This quantity can preferably be expressed in toxin units, with one toxin unit corresponding to the dose which results in the death of 50% of the animals tested.

Preferably, the method according to the invention is a method for determining the $LD_{50}$ of a sample containing the botulinum toxin.

Also very preferably, this is a method for determining the $LD_{50}$ of the botulinum toxin, preferably botulinum toxin of type A, comprising the following stages:
 (i) injecting the botulinum toxin into at least one zebra fish;
 (ii) detecting the biological activity of the botulinum toxin;
 (iii) comparing the effect obtained in stage (ii) to the effect obtained with a reference botulinum toxin;
 (iv) determining the $LD_{50}$ of the botulinum toxin.

According to another very preferable variant, the method according to the invention is a method for determining the kinetics action of the botulinum toxin comprising the following stages:
 (i) injecting the botulinum toxin into at least one zebra fish;
 (ii) detecting the biological activity of the botulinum toxin as a function of time.

The following examples illustrate the invention without limiting its scope.

EXAMPLES

The botulinum toxin used in these examples was obtained from Ipsen. It was a batch of Dysport®.

A negative control was carried out using a non-toxic protein, bovine serum albumin (BSA).

1/ Injection of the Zebra Fish:

The Dysport® was made up in solution as follows: 3 mg of Dysport® equivalent to 580 units was dissolved in 26 µl of deionized water to give a concentration of 115 mg/ml (22,000 U/ml). This solution was diluted four times in order to obtain a 28.75 mg/ml solution: i.e. 5,500 U/ml.

The BSA was made up in solution at a concentration of 115 mg/ml and 28.75 mg/ml in deionized water.

The 5 or 21-day-old zebra fish were injected by intra-peritoneal route with the Dysport® to be tested:
 10 to 20 nl of test solution for the 5-day-old fish;
 40 to 80 nl of test solution for the 21-day-old fish.

Figure 1:
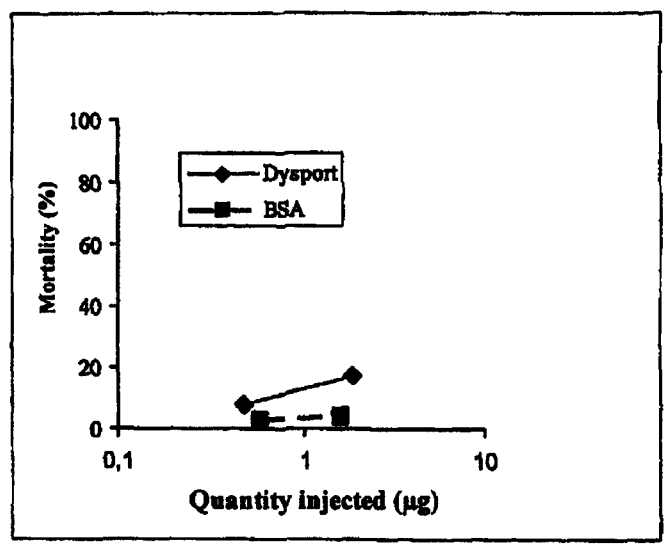
FIG. 1 represents the mortality of 5-day-old zebra fish as a function of the quantities of botulinum toxin injected.

2/ Results:

2-1 Method for Determining a Quantity of Dysport® with 5-Day-Old Zebra Fish:

Thirty zebra fish received an intra-peritoneal injection of Dysport®. The fish were fed daily and the aquarium water was changed regularly. The fish mortality was observed 4 days after the injection. The results are shown in Table I below and in FIG. 1.

TABLE I

|  | Quantity Injected (µg) | |
| --- | --- | --- |
| BSA | 0.58 | 1.6 |
| Mortality (%) | 3 | 4 |
|  | Quantity Injected (µg) | |
| DYSPORT ® | 0.46 | 1.84 |
| Mortality (%) | 8 | 17 |

Figure 2:
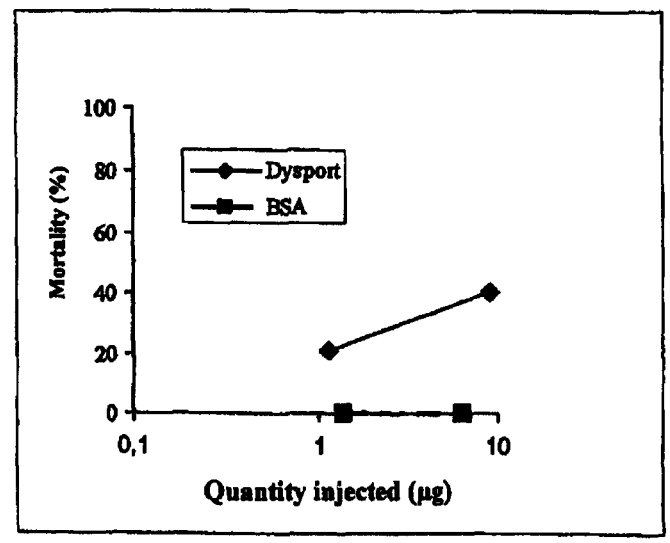
FIG. 2 represents the mortality of 21-day-old zebra fish as a function of the quantities of botulinum toxin injected.

2-2 Method for Determining a Quantity of Dysport® with 21-Day-Old Zebra Fish:

Twenty zebra fish received an intra-peritoneal injection of Dysport®. The fish were fed daily and the aquarium water was changed regularly. The results are shown in Table II below and in FIG. 2.

TABLE II

|  | Quantity Injected (µg) | |
| --- | --- | --- |
| BSA | 1.4 | 6.55 |
| Mortality (%) | 0 | 4 |
|  | Quantity Injected (µg) | |
| DYSPORT ® | 1.15 | 9.2 |
| Mortality (%) | 21 | 41 |

2-3 Conclusion:

This method enables a dose-dependant activity of the botulinum toxin to be demonstrated in comparison to a reference protein BSA.

2-4 Method for Determining the Kinetics of Dysport® with 21-Day-Old Zebra Fish:

After 24 hours, the zebra fish treated with Dysport® showed a marked neuromuscular impairment.

After 48 hours, 20% of the treated zebra fish were still completely paralyzed, the others being unable to swim and their movements limited to weak, uncoordinated movements of the caudal fin. Similar effects were noted in 5-day-old and 21-day-old zebra fish. However, administration of Dysport® did not remove the ability of the fish to remain vertical.

After 3 days, the fish recovered partial mobility and 4 days after administration of the cholinergic neurotoxin, total recovery had taken place.

The invention claimed is:

1. A method for determining the concentration of botulinum neurotoxin sample comprising the following steps:
 (a) administering the botulinum neurotoxin sample to at least one Zebra fish by intraperitoneal injection;
 (b) detecting the neuromuscular activity of the botulinum neurotoxin sample,
  wherein the neuromuscular activity is slowing of mobility, reduction in motility, immobility, paralysis, or a combination thereof;
 (c) comparing the neuromuscular activity determined in step (b) to the neuromuscular activity of botulinum neurotoxin of known concentration; and
 (d) determining the concentration of the botulinum neurotoxin sample.

2. The method of claim 1, wherein the botulinum neurotoxin is a protein, a polypeptide, a peptide, a fusion protein, a truncated protein, a chimeric protein, a mutated protein, or a recombinant protein.

3. The method of claim 1, wherein the botulinum neurotoxin administered in step (a) is combined with a fatty acid.

4. The method of claim 1, wherein the Zebra fish is a fish with a wild phenotype, a mutant phenotype, or a transgenic fish.

5. The method of claim 1, wherein one or more Zebra fish are present in a microtitration well of an automatic device.

6. The method of claim 1, wherein step (b) is carried out with an image analyzer.

7. The method of claim 1, wherein the neuromuscular activity is a muscular paralysis.

8. The method of claim 1, wherein the botulinum neurotoxin is the botulinum neurotoxin of type A, type B, type C, type D, type E, type F, or type G.

9. A method for determining the concentration of botulinum neurotoxin sample comprising:
   (a) administering the botulinum neurotoxin sample to at least one Zebra fish by intraperitoneal injection;
   (b) detecting the biological activity of the botulinum neurotoxin sample, wherein the biological activity is slowing of mobility, reduction in motility, immobility, difference in the behavior of the fish, or a combination thereof;
   (c) comparing the biological activity determined in step (b) to the biological activity of botulinum neurotoxin of known concentration; and
   (d) determining the concentration of the botulinum neurotoxin sample.

* * * * *

UNITED STATES PATENT AND TRADEMARK OFFICE
CERTIFICATE OF CORRECTION

PATENT NO. : 9,176,119 B2
APPLICATION NO. : 12/065523
DATED : November 3, 2015
INVENTOR(S) : Jose-Antonio Camara Y. Ferrer et al.

Page 1 of 1

It is certified that error appears in the above-identified patent and that said Letters Patent is hereby corrected as shown below:

Item (75), first inventors name "Jose-Antonio Camara-Ferrer" should read --Jose-Antonio Camara Y. Ferrer--.

Item (75), second inventors name "Michael Auguet" should read --Michel Auguet--.

Signed and Sealed this
Twenty-second Day of March, 2016

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 9,176,119 B2 |
| APPLICATION NO. | : 12/065523 |
| DATED | : November 3, 2015 |
| INVENTOR(S) | : Jose-Antonio Camara Y. Ferrer et al. |

It is certified that error appears in the above-identified patent and that said Letters Patent is hereby corrected as shown below:

ON THE TITLE PAGE

Item (12), should read --Camara Y. Ferrer et al.--.

Signed and Sealed this
Twenty-ninth Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,176,119 B2  
APPLICATION NO. : 12/065523  
DATED : November 3, 2015  
INVENTOR(S) : Jose-Antonio Camara Y. Ferrer et al.

Page 1 of 1

It is certified that error appears in the above-identified patent and that said Letters Patent is hereby corrected as shown below:

Title Page:

Item (12), should read --Camara Y. Ferrer et al.--.

Item (75), first inventors name "Jose-Antonio Camara-Ferrer" should read --Jose-Antonio Camara Y. Ferrer--.

Item (75), second inventors name "Michael Auguet" should read --Michel Auguet--.

This certificate supersedes the Certificate of Correction issued March 22, 2016.

Signed and Sealed this  
Twelfth Day of July, 2016

Michelle K. Lee  
*Director of the United States Patent and Trademark Office*